United States Patent
Ray et al.

(10) Patent No.: US 6,599,267 B1
(45) Date of Patent: Jul. 29, 2003

(54) TRANSLUMINAL INJECTION DEVICE FOR INTRAVASCULAR DRUG DELIVERY

(75) Inventors: Pinaki Ray, Fremont, CA (US); Henri A. Gaudoin, Mountain View, CA (US); Lyudmila K. Kokish, Los Gatos, CA (US); Arkady Kokish, Los Gatos, CA (US); Daryush Mirzaee, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 107 days.

(21) Appl. No.: 09/746,862

(22) Filed: Dec. 22, 2000

(51) Int. Cl.⁷ .................................. A61M 25/00
(52) U.S. Cl. ..................... 604/102.01; 604/103.01; 604/264; 604/109
(58) Field of Search ............... 604/102.01, 96.01, 604/102.02, 103.03, 164.01, 164.03, 164.12, 264, 272, 274, 523, 528, 915, 606, 194, 192, 97.01, 97.02, 104, 27, 48, 93.01, 105, 106, 107, 108

(56) References Cited

U.S. PATENT DOCUMENTS

| | | | | |
|---|---|---|---|---|
| 5,354,279 A | | 10/1994 | Höfling | 604/164 |
| 5,419,777 A | * | 5/1995 | Höfling | 604/264 |
| 5,545,209 A | * | 8/1996 | Roberts et al. | 623/1.11 |
| 5,693,029 A | | 12/1997 | Leonhardt | 604/264 |
| 5,707,358 A | * | 1/1998 | Wright | 604/103.07 |
| 5,746,716 A | | 5/1998 | Vigil et al. | 604/97 |
| 6,217,554 B1 | * | 4/2001 | Green | 604/164.01 |
| 6,270,504 B1 | * | 8/2001 | Lorentzen Cornelius et al. | 606/108 |
| 6,270,521 B1 | * | 8/2001 | Fischell et al. | 623/1.11 |
| 6,283,947 B1 | * | 9/2001 | Mirzaee | 604/264 |
| 6,302,870 B1 | * | 10/2001 | Jacobsen et al. | 604/272 |
| 6,395,008 B1 | * | 5/2002 | Ellis et al. | 606/108 |

\* cited by examiner

Primary Examiner—Henry C. Yuen
Assistant Examiner—Hai Huynh
(74) Attorney, Agent, or Firm—Blakely, Sokoloff, Taylor & Zafman LLP

(57) ABSTRACT

A catheter including an injection port at or near the distal end thereof and a mechanism for causing the injection port to move between a first position and a second position. In the first position the injection port is substantially aligned with a central axis of the catheter. Upon activation of the mechanism, the injection port moves between the first position and the second position perpendicular to the central axis of the catheter. The mechanism also causes the injection port to move away from the central axis of the catheter and into a wall of the vasculature.

19 Claims, 11 Drawing Sheets

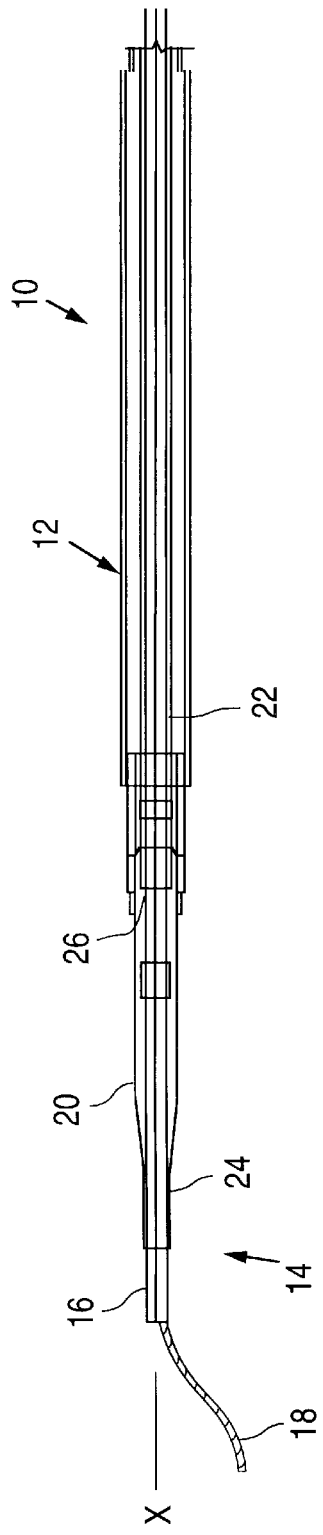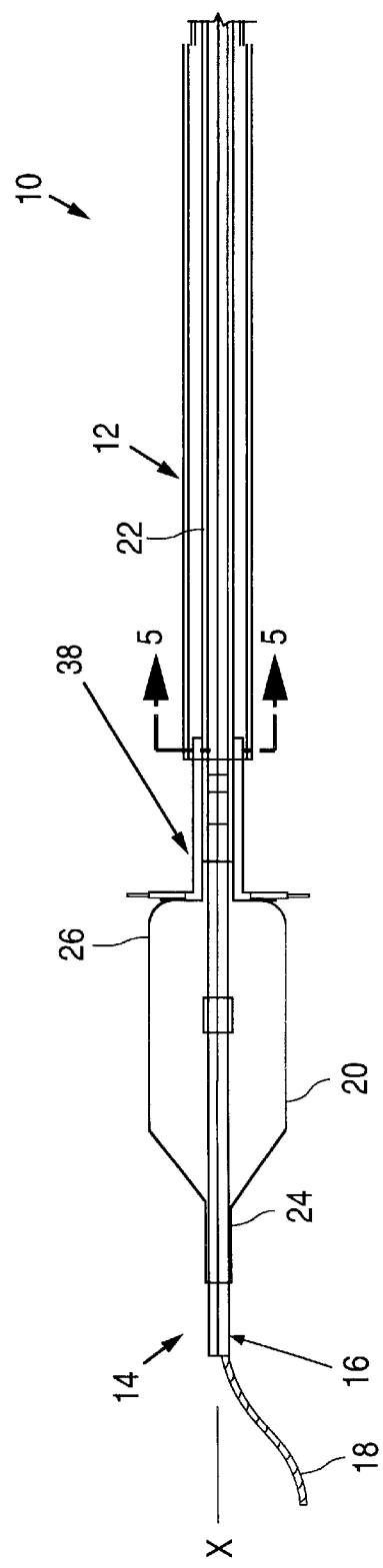

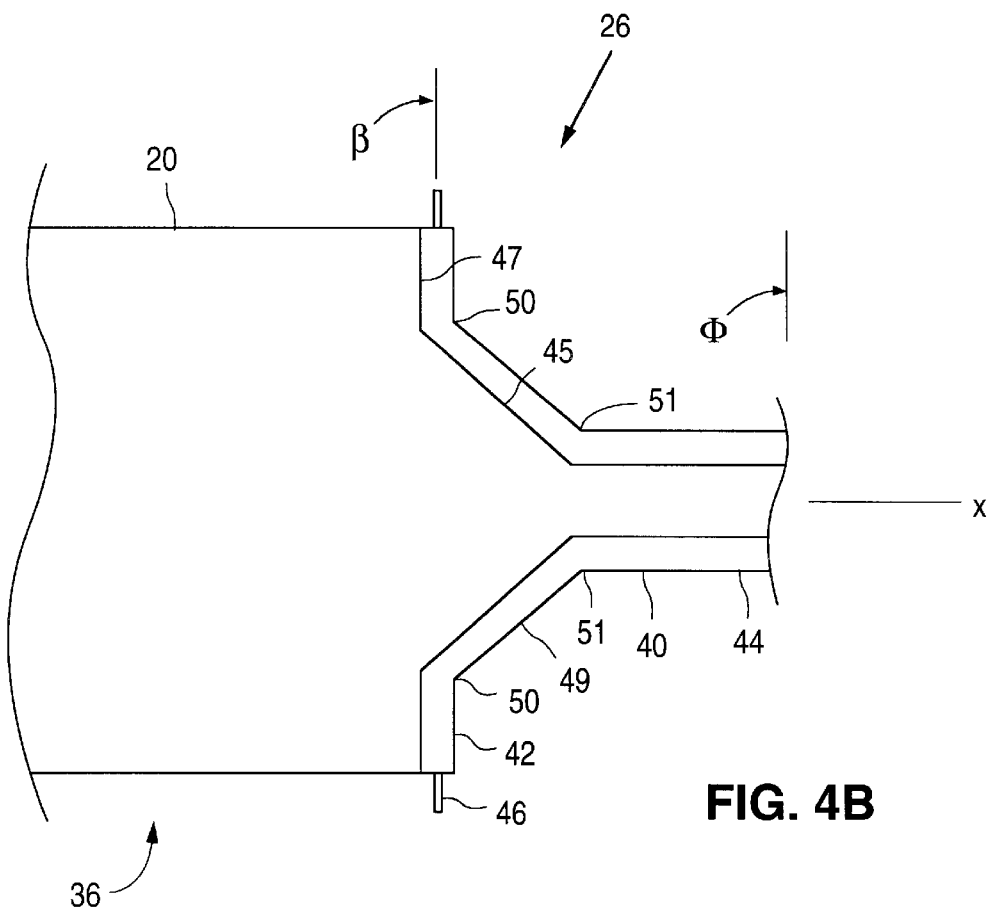
FIG. 4B
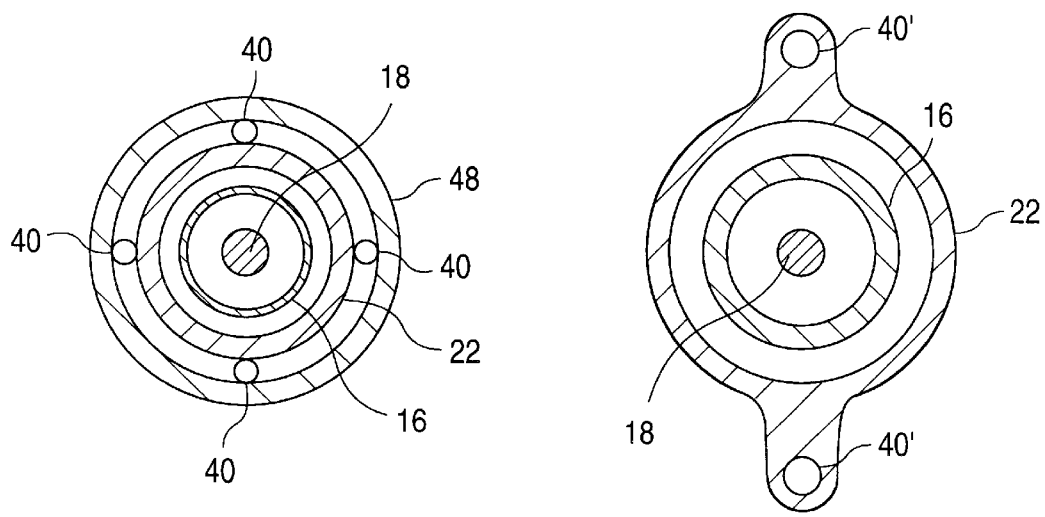
FIG. 5  FIG. 6B

US 6,599,267 B1

TRANSLUMINAL INJECTION DEVICE FOR INTRAVASCULAR DRUG DELIVERY

BACKGROUND OF THE INVENTION

1. Field of the Invention

The present invention relates to a medical device for delivering a substance to a vascular lumen. In particular, the invention relates to a catheter for delivering and/or withdrawing a therapeutic substance to a location within a vascular lumen.

2. Related Art

Percutaneous transluminal coronary angioplasty (PTCA) is a procedure for treating heart disease. Typically, a catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion against the inner wall of the artery to dilate the lumen. The balloon is then deflated to a smaller profile to allow the catheter to be withdrawn from the patient's vasculature.

Restenosis of the artery commonly develops over several months after the procedure, which may require another angioplasty procedure or a surgical by-pass operation. Restenosis is thought to involve the body's natural healing process. Angioplasty or other vascular procedures injure the vessel walls, removing the vascular endothelium, disturbing the tunica intima, and causing the death of media smooth muscle cells. Excessive neointimal tissue formation, characterized by smooth muscle cell migration and proliferation to the intima, follows the injury. Proliferation and migration of smooth muscle cells (SMC) from the media layer to the intima cause an excessive production of extra cellular matrices (EM), which is believed to be one of the leading contributors to the development of restenosis. The extensive thickening of the tissues narrows the lumen of the blood vessel, con stricting or blocking blood flow through the vessel.

To reduce the chance of the development of restenosis, therapeutic substances are administered to the treatment site. For example, anticoagulant and antiplatelet agents are commonly used to inhibit the development of restenosis. To supply an efficacious concentration to the target site requires a systemic administration of such medication in quantities which often produces adverse or toxic side effects for the patient. Local delivery is a preferred method of treatment in that smaller total levels of medication are administered in comparison to systemic dosages, but are concentrated at a specific site. Local delivery, thus, produces fewer side effects and achieves more effective results.

SUMMARY

The present invention provides a catheter for delivery of a therapeutic substance to a target location in a patient's vasculature. The catheter supplies an efficacious concentration of the therapeutic substance to the target site, which reduces the total levels of medication required to be administered to patients relative to typical systemic dosages. The concentrated delivery of the therapeutic substance produces fewer side effects and achieves more effective results.

In one aspect of the invention, the catheter includes an injection port at or near the distal end thereof and a surface for applying a force to cause the injection port to move between a first position and a second position in the first position the injection port is substantially aligned with a central axis of the catheter. Upon application of the force, the injection port moves between the first position and the second position perpendicular to the central axis of the catheter. Advantageously, an additional force can be applied which causes the injection port to move to a third position away from the central axis of the catheter and into a wall of the vasculature. Advantageously, the injection port is a hollow needle disposed at the end of a substance delivery lumen.

In another aspect, a method is provided for delivering medication to a patient. The method includes delivering at least one injection port to a location within a human vasculature. The injection port is coupled to a substance delivery lumen. The injection port is moved between a first position and a second position to inject medication into the patient through the substance delivery lumen and the injection port.

Uses, advantages, and variations of the present invention will be apparent to one of ordinary skill in the art upon reading this disclosure and accompanying drawings.

BRIEF DESCRIPTION OF THE DRAWINGS

FIG. 1A is a partial sectional view of one embodiment of a substance delivery apparatus in the form of a catheter assembly having a balloon in a collapsed configuration;

FIG. 1B is a partial sectional view of the delivery apparatus of FIG. 1A, illustrating the balloon in an expanded configuration;

FIGS. 4A and 4B are simplified side views of alternative embodiments of the balloon in FIGS. 1A and 1B in accordance with the present invention;

FIG. 5 is a simplified cross-sectional view of the delivery apparatus shown in FIG. 1B;

FIG. 6B is a cross-sectional view of FIG. 6A;

DETAILED DESCRIPTION

Figure 2:
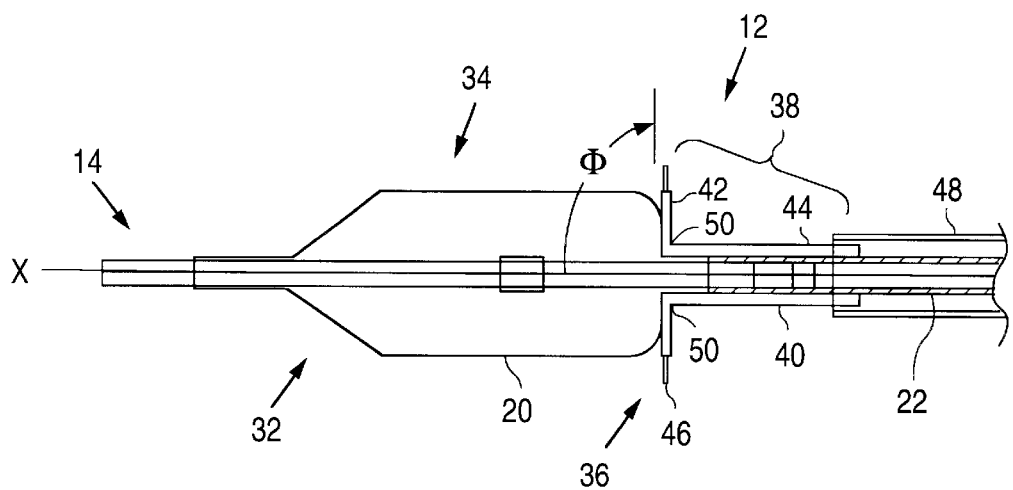
FIG. 2 is a magnified view of a distal end of the delivery apparatus shown in FIG. 13.

Referring now to the drawings, where similar parts are identified by like reference numerals, FIGS. 1A and 1B are sectional views of a substance delivery apparatus 10 in accordance with one embodiment of the invention. In general, substance delivery apparatus 10 provides for delivering a substance, such as a therapeutic substance or a combination of therapeutic substances, to or through a desired area of a vascular lumen to treat a localized area of the vascular lumen or to treat a localized area of tissue located adjacent to the vascular lumen. Substance delivery apparatus 10 includes a catheter assembly 12, which is intended to include any angioplasty device design used for insertion into a body passageway to permit injection and/or withdrawal of fluids, to maintain the patency of the passageway, or for any other purpose. It is contemplated that substance delivery apparatus 10 has applicability for use with any biological passageway, including blood vessels, urinary tract, intestinal tract, kidney ducts, wind pipes, and the like.

Catheter assembly 12 is encased by an elongated member having a proximal end (not illustrated) and distal end 14. Catheter assembly 12 can include an inner member 16 which provides a guidewire lumen for allowing catheter assembly 12 to be fed and maneuvered over a guidewire 18. A balloon 20 is incorporated at distal end 14 of catheter assembly 12 and is in fluid communication with an outer member 22, which provides an inflation lumen to inflate balloon 20. The proximal end of catheter assembly 12 includes conventional features which are well-known and understood by one of ordinary skill in the art for the proper functioning of catheter assembly 12.

In one embodiment, balloon 20 has a pair of opposing ends 24 and 26. Balloon 20 can be formed from a balloon wall or membrane, which is selectively inflatable to dilate from a collapsed configuration (FIG. 1A) to a desired and controlled expanded configuration (FIG. 1B). Balloon 20 can be selectively inflated by supplying a fluid into inflation lumen 22 at a predetermined rate of pressure, for example 1–20 atm. Balloon 20 is selectively deflatable, after inflation, to return to the collapsed configuration or a deflated profile.

FIG. 2 is a magnified view of distal end 14 of catheter assembly 12. As shown, balloon 20 can be defined by three portions, a distal portion 32, a medial portion 34, and a proximal portion 36. Proximal portion 36 of balloon 20 can taper from opposing end 26 at any suitable angle $\Phi$, for example, between about 45° to about 90°, when balloon 20 is in the expanded configuration. In one embodiment, the taper may be made substantially perpendicular to a longitudinal axis x of balloon 20 (i.e., $\Phi$ equal to about 90°) when balloon 20 is in the expanded configuration.

The three portions 32, 34, and 36 can be bound together by seams or be made out of a single seamless material. Balloon 20 can be made from any suitable material, as long as the specific material employed is mutually compatible with the fluids employed in conjunction with balloon 20 and able to withstand the inflation pressure developed within balloon 20. For example, balloon 20 may be made from, but not limited to, polymers and copolymers of polyolefins, polyamides, polyesters and the like. The balloon wall can have any suitable constant or variable thickness so long as the thickness does not compromise properties that are critical for achieving optimum performance. The properties include high burst strength, low compliance, good flexibility, high resistance to fatigue, the ability to fold, the ability to cross and recross a desired region of treatment or an occluded region in the vascular lumen, and low susceptibility to defect caused by handling.

By way of example, and not limitation, the thickness can be in the range of about 10 microns to about 30 microns, the diameter of balloon 20 in the expanded configuration can be in the range of about 2 mm to about 10 mm, and the length can be in the range of about 3 mm to about 40 mm, the specific specifications depending on the procedure for which balloon 20 is to be used and the anatomy and size of the target lumen in which balloon 20 is to be inserted.

Again referring to FIG. 2, catheter assembly 12 includes at least one injection port assembly 38 or a plurality of injection port assemblies 38 for injecting therapeutic substances into a tissue of a biological lumen. Each injection port assembly 38 includes a hollow substance delivery lumen 40, having a distal section 42 and a proximal section 44, and a hollow needle 46 for penetrating into the tissue of the biological lumen. Substance delivery lumen 40 can be made from any suitable material, such as polymers and copolymers of polyamides, polyolefins, polyurethanes, and the like. Needle 46 can be made of any suitable material, for example, stainless steel.

In one embodiment, proximal section 44 of substance delivery lumen 40 is in fluid communication with a substance delivery sheath 48. Distal section 42 of substance delivery lumen 40 is in fluid communication with hollow needle 46. A portion of needle 46 which protrudes from lumen 40 for insertion into the biological lumen can be of any predetermined length, the specific length being dependent upon the desired depth of calibrated penetration and the procedure for which injection port assembly 38 is to be used. In one embodiment, the needle length can be from about 250 microns to about 3 mm. Needle 46 can have an inner diameter of about 0.05 mm to about 0.25 mm and an outer diameter of about 0.12 mm to about 0.35 mm.

In a first position or collapsed configuration of balloon 20 (FIG. 1A), needle 46 of injection port assembly 38 is disposed longitudinally and substantially parallel to longitudinal axis x of balloon 20. Distal section 42 of substance delivery lumen 40 is capable of rotating about a bending point or elbow 50 with respect to proximal section 44. Distal section 42 of substance delivery lumen 40 contacts proximal portion 36 of balloon 20, and accordingly, needle 46 can be made to rotate about elbow 50 in response to the expansion and retraction of balloon 20.

The dilation of balloon 20 pivots needle 46 of injection port assembly 38 towards a second position or substantially perpendicular to axis x. The extent of the rotation of distal section 42 is dependent upon the angle $\Phi$ at which proximal portion 36 of balloon 20 tapers from end 26 when balloon 20 is in the expanded configuration.

Figure 3A:
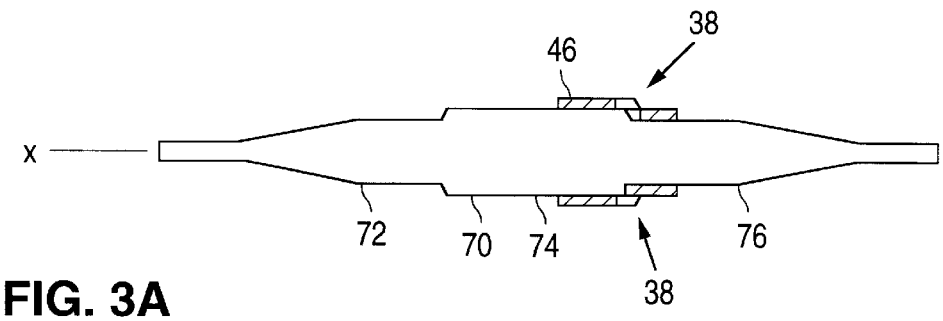
FIGS. 3A–3C are simplified section al views of an embodiment of the balloon in FIGS. 1A and 1B in accordance with the present invention.
Figure 3B:
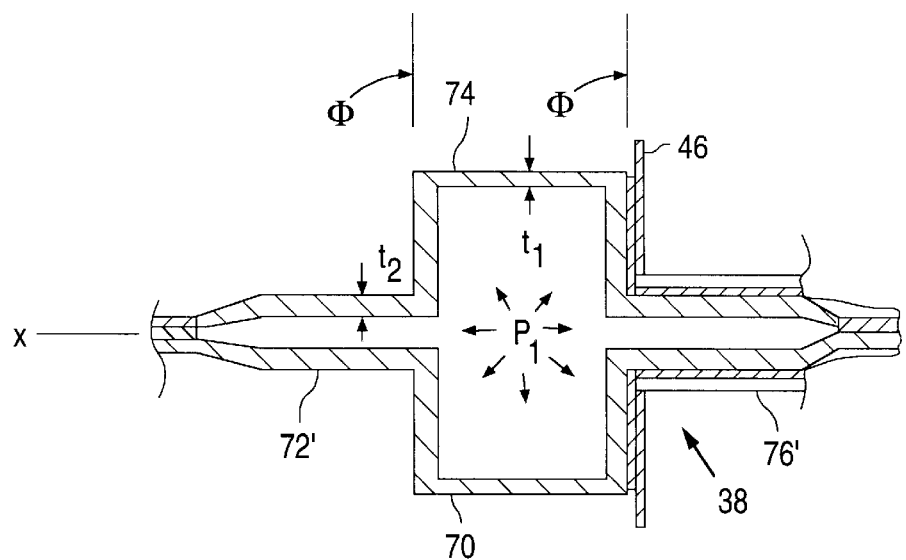
Figure 3C:
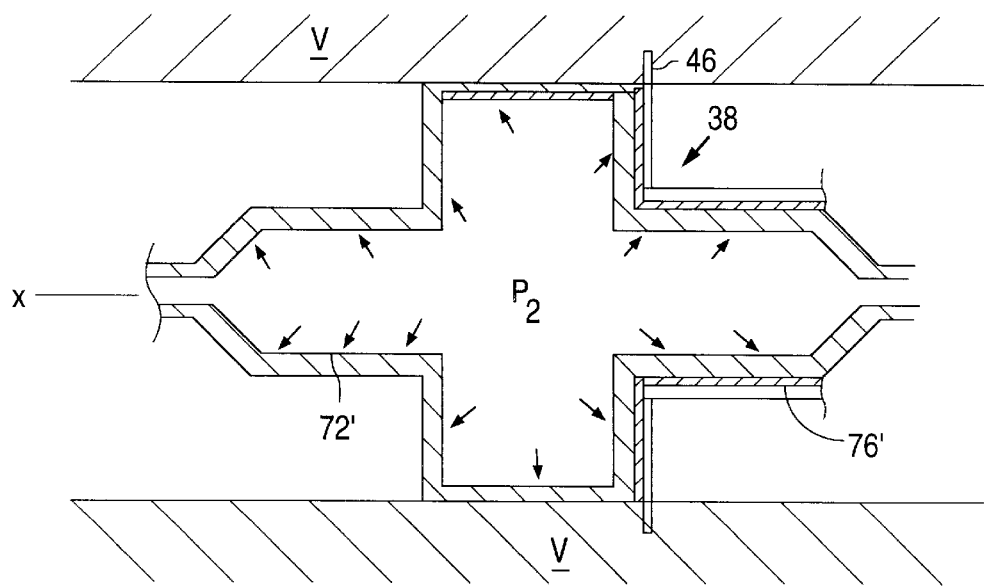

A FIG. 3A is a side view and FIGS. 3B and 3C are sectional views of another embodiment of balloon 70 of delivery apparatus 10 (FIGS. 1A–B). As shown in FIG. 3A, balloon 70 can be defined by three portions, a distal portion 72, a medial portion 74, and a proximal portion 76. As illustrated in FIG. 3B, the wall of balloon 70 is designed with variable thickness across the working length. By way of example, and not limitation, the wall thickness $t_2$ at distal portion 72 and proximal portion 76 (hereinafter "tails 72' and 76'", respectively) can be made thicker than the wall thickness $t_1$ in the medial portion 74. In one embodiment, wall thickness $t_2$ of tails 72' and 76' can be in the range of about 2 to 4 times wall thickness $t_1$ of medial portion 74. For example, medial portion 74 may have wall thickness $t_1$ of about 10 microns, while tails 72' and 76' have wall thickness $t_2$ of about 30 microns.

In a first position or collapsed configuration of balloon 70 (FIG. 3A), needle 46 of injection port assembly 38 is disposed longitudinally and substantially parallel to longitudinal axis x of balloon 70. In operation, balloon 70 can be inflated to a first pressure, which is sufficient to overcome the balloon tension created by wall thickness $t_1$, to cause medial portion 74 to expand (FIG. 3B). Tails 72' and 76' remain under-inflated since the first pressure is selectively insufficient to overcome the balloon tension created by wall thickness $t_2$. Expansion of medial portion 74 causes needle 46 of injection port assembly 38 to rotate towards a second position, which is substantially perpendicular to axis x.

Once needle 46 is in the second position, balloon 70 can be further inflated to a second pressure. The second pressure is sufficient to overcome the balloon tension created by wall thickness $t_2$ and inflates tails 72' and 76' (FIG. 3C). The expansion of tails 72' and 76' causes injection port assembly 38 to move away from axis x to a third position causing needle 46 to pierce vascular wall V.

After the therapeutic substance has been delivered or as desired, balloon 70 can be deflated to the first pressure, thus allowing the balloon tension in tails 72' and 76' to cause port assembly 38 to move toward axis x and remove needle 46 from vascular wall V. Balloon 70 can be further deflated to return needle 46 to the first position so the catheter assembly can be moved through the vasculature.

Figure 4A:
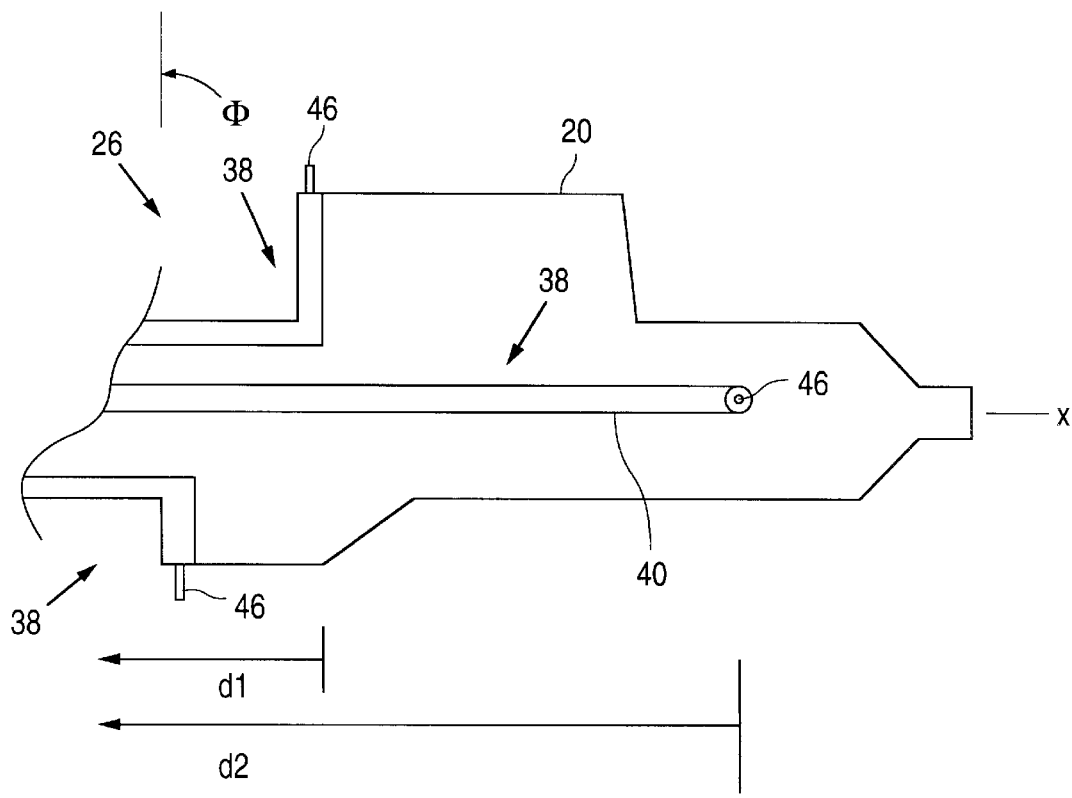

FIG. 4A illustrates a simplified side view of an alternative embodiment of balloon 20, in which balloon 20 can be formed having multiple tapered surfaces. The multiple tapered surfaces can extend from end 26 along the entire working length of balloon 20. In one embodiment, the multiple tapers can extend variable distances from end 26, such as a distance $d_1$ and $d_2$ to ensure an adequate circumferential distribution of needles 46 and an adequate axial distribution of the therapeutic substance. Each tapered surface can be in contact with an injection port assembly 38, such that the dilation of balloon 20 pivots needle 46 of injection port assembly 38 towards a second position at an angle to axis x. The extent of the rotation of distal section 42 is dependent upon the angle $\Phi$ at which proximal portion 36 of balloon 20 tapers from end 26 when balloon 20 is in the expanded configuration. The tapers can be at any suitable angle $\Phi$, typically from 0° up to about 45°.

FIG. 4B illustrates a simplified sectional view of an alternative embodiment of balloon 20 in which proximal portion 36 can include a stepped taper formed at end 26. The stepped taper includes an initial taper 45, which can extend any desired length from end 26, at any suitable angle $\phi$, typically between about 45° to about 90°, when balloon 20 is in the expanded configuration. Initial taper 45 terminates with a final taper 47, which can also have any suitable angle $\Phi$, typically between about 45° to about 90°, when balloon 20 is in the expanded configuration.

In the first position or collapsed configuration of balloon 20 (FIG. 1A), needle 46 of injection port assembly 38 is disposed longitudinally and substantially parallel to longitudinal axis x of balloon 20. As shown in FIG. 4B, distal section 42 and a medial section 49 of substance delivery lumen 40 are capable of rotating about bending points or elbows 50 and 51, respectively, with respect to proximal section 44. Medial section 49 of substance delivery lumen 40 contacts initial taper 45 while distal section 42 of substance delivery lumen 40 contacts final taper 47 of balloon 20. In response to the expansion of balloon 20, medial section 49 of substance delivery lumen 40 rotates about elbow 51 an angle equivalent to the angle of initial taper 45. Distal section 42, including needle 46, rotates about elbow 50 an angle equivalent to the angle of final taper 47. Thus, the dilation of balloon 20 pivots needle 46 of injection port assembly 38 towards a second position, which can be for example, at any angle up to substantially perpendicular to axis x. This alternative embodiment can allow for ease of folding when balloon 20 is deflated and can provide a lower profile to facilitate insertion of apparatus 10 into the human vascular system.

As shown in FIG. 2, substance delivery apparatus 10 can include any suitable number of injection port assemblies 38, disposed about the periphery of balloon 20 and in communication with a portion 32, 34, and 36. Each of injection port assemblies 38 can communicate with a respective, designated substance delivery sheath 48. FIG. 5 is a cross-sectional view of delivery sheath 48, which can be disposed circumferentially and concentrically about inner member 16 and outer member 22. Substance delivery lumens 40, a plurality of which are illustrated, can be in fluid communication with one another and/or in fluid communication with a common source of supply of a therapeutic substance through drug delivery sheath 48. Thus, each of injection port assemblies 38 can be capable of injecting the same therapeutic substance or the same combination of therapeutic substances.

Figure 6A:
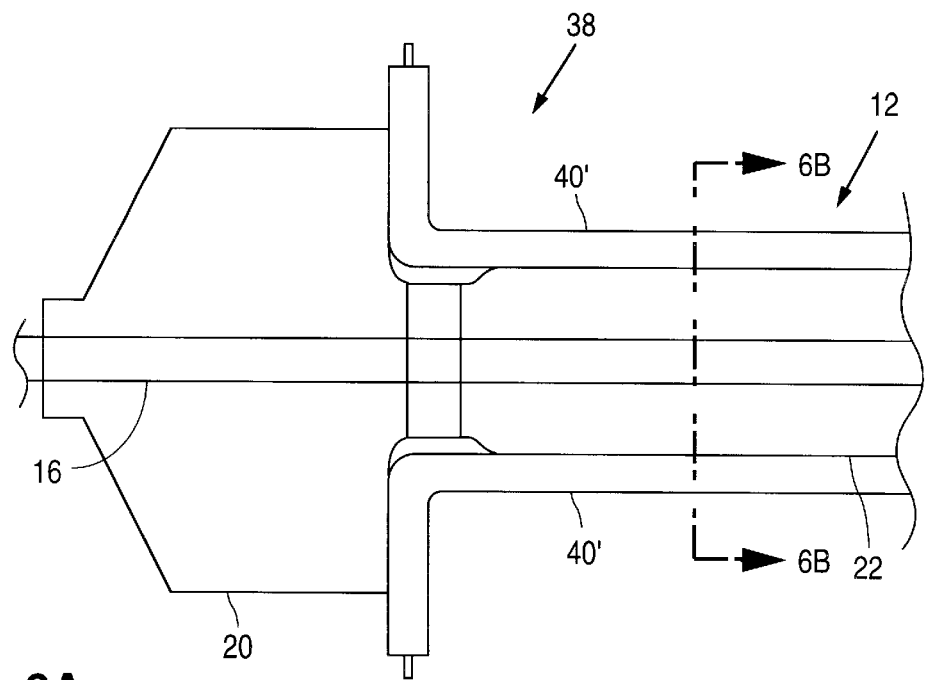
FIG. 6A is a simplified side-sectional view of a portion of the delivery apparatus.

FIGS. 6A and 6B are simplified illustrations of a sectional and a cross-sectional view, respectively, of the delivery apparatus in accordance with an alternative embodiment, in which each substance delivery lumen 40' is an independent lumen, which can independently supply each needle 46 from a different source of the therapeutic substance or with different combinations of substances. In this alternative embodiment, each substance delivery lumen 40' extends the length of catheter assembly 12. Although FIG. 6B illustrates two mutually independent lumens 40', any number of substance delivery lumens for delivering the therapeutic substance can be used, for example, between two and six lumens. However, the invention is not limited by the exact number of substance delivery lumens 40'.

Substance delivery lumens 40' are in fluid communication with a therapeutic substance delivery port (not shown) positioned at the proximal end of catheter assembly 12. The substance delivery port can receive a drug or medication which is to be injected into the patient. The therapeutic substance delivery port is also in fluid communication with a pressurized supply source 56 (FIG. 7), such as a syringe or similar device, which may be manually manipulated to deliver a substance into the delivery port.

Figure 7:
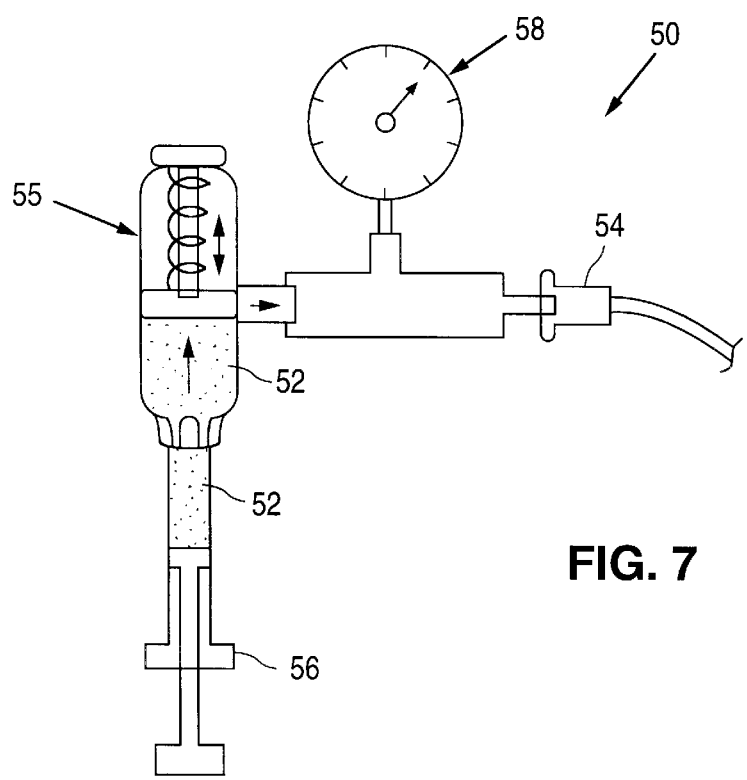
FIG. 7 is a simplified illustration of a pressurized delivery source.

In an embodiment illustrated in FIG. 7, a check valve or relief valve 50, can be coupled to pressurized supply source 56 to ensure that the pressurized supply source delivers measured amounts of therapeutic substance 52 to the therapeutic delivery port via adapter 54. Valve 50 includes pressurized supply source 56 coupled in-line with a flow limiting device 55 and a pressure gage 58. In one embodiment, flow limiting device 55 provides for stopping fluid flow from pressurized supply source 56. For example, valve 50 can be designed such that in normal operation flow limiting device 55 is closed allowing no fluid flow. Upon activation of pressurized supply source 56, flow limiting device 55 remains closed until supply source 56 reaches a threshold pressure, for example, about 80 psi. Once pressure gage 58 senses that the threshold pressure has been achieved, valve 50 opens to allow therapeutic substance 52 to flow to substance delivery lumens 40' (FIG. 6A). Each independent substance delivery lumen 40' can be in fluid communication with the same valve 50 or an independent valve 50, such that each injection port assembly 38 can function independently and each needle 46 can deliver therapeutic substance 52 independent of the other needles.

Fluid flow from valve 50 can be under such pressure that the pressure causes therapeutic fluid 52 to break through the vascular wall and infiltrate the surrounding tissue. If a break through of the vascular wall occurs, gage 58 in valve 50 senses a drop in pressure since the therapeutic substance is no longer confined to the vascular lumen. Once the pressure drops below the threshold pressure, flow limiting device 55 closes which stops the flow of therapeutic substance 52 and prevents injury to the vascular tissue. Beneficially, since each substance delivery lumen 40' is fed the therapeutic substance through a different valve 50, the flow of therapeutic substance to each of the other substance delivery lumens 40' continues uninterrupted.

In an alternative embodiment, valve 50 can be in fluid communication with therapeutic substance delivery sheath 48 (FIG. 2). In this embodiment, the delivery of the therapeutic substance through injection port assemblies 38 is controlled via delivery sheath 48.

Although valve 50 is described herein for use with a manual pressurized supply source 56, valve 50 can be used with an automatic pressurized supply source, such as a drug pump or continuous IV source.

Figure 8A:
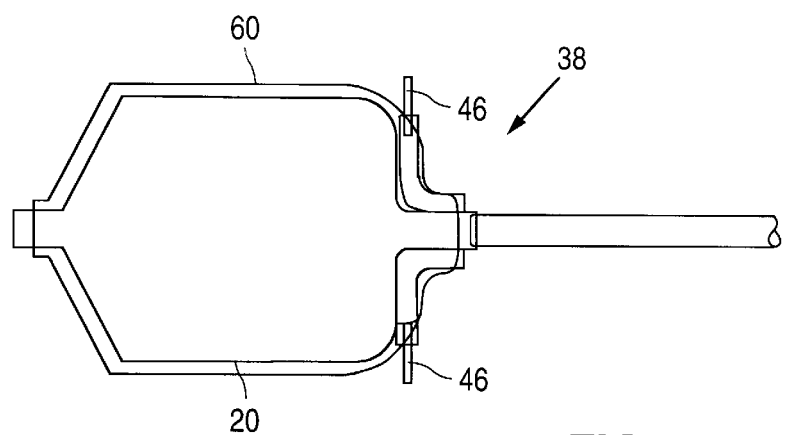
FIGS. 8A and 8B are simplified illustrations of the delivery apparatus of FIG. 1B including an elastomeric sleeve.
Figure 8B:
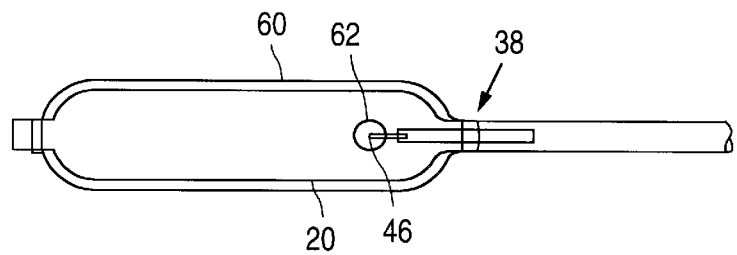

FIGS. 8A and 8B show top and side views, respectively, of catheter assembly 12 of FIG. 2 used in conjunction with an elastomer membrane or sleeve 60. In one embodiment, sleeve 60 may be used to surround a portion of catheter body 12, including injection port assemblies 38 and balloon 20. Sleeve 60 can be adhesively bonded to catheter assembly 12 using and adhesive, such as Dymax. Sleeve 60 keeps needles 46 close to catheter assembly 12 to ensure a low profile, and ensure that needles 46 stay aligned with the longitudinal axis x of catheter assembly 12 during deployment. As balloon 20 is expanded, sleeve 60 also expands (i.e., stretches) to allow injection port assemblies 38 to function as described above. Sleeve 60 can be formed with holes 62 to allow needles 46 to extend through sleeve 60 during the expansion of balloon 20 in the vasculature. When balloon 20 is deflated, the superelastic nature of sleeve 60 provides a force for returning injection port assemblies 38 to their longitudinally aligned position. Sleeve 60 may be made of any suitable material, such as polyurethane, latex, or silicone. The inner diameter of sleeve 60 may range from about 0.02" to about 0.0525" with an outer diameter of between about 0.04" to about 0.06". For example, sleeve 60 can be made of Carbothane 75A PC 35550 with an OD of 0.048" and an ID of 0.0405".

Figure 9A:
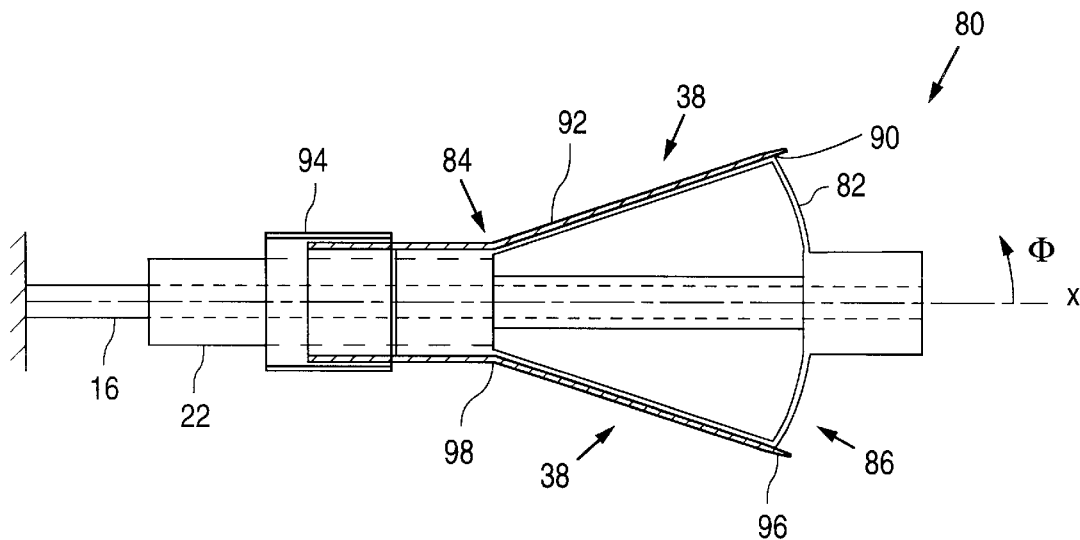
FIGS. 9A–9D illustrate another embodiment of the therapeutic delivery apparatus.
Figure 9B:
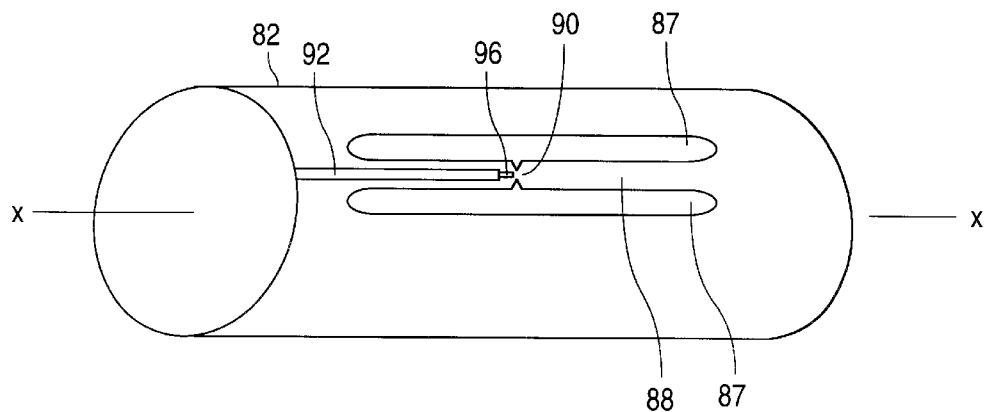

FIGS. 9A–9E illustrate sectional views of another embodiment of therapeutic delivery apparatus 80. Therapeutic delivery apparatus 80 includes an expandable member 82 having a proximal end 84 and a distal end 86. Expandable member 82 is disposed on a distal end of catheter body 12. In this embodiment, expandable member 82 can be a superelastic tubing, which can be made of any suitable material, such as stainless steel or NiTi. As shown in FIG. 9B, expandable tubing 82 can have a pattern of one or more slots 87 cut or formed circumferentially into tubing 82. The material remaining between each slot creates a support member or strut 88. Each strut 88 can be designed to include a point of inflexion 90. For example, point of inflexion 90 can be formed by removing a small amount of material from each strut 88, forming opposed triangular cut-outs or indentation.

Figure 9C:
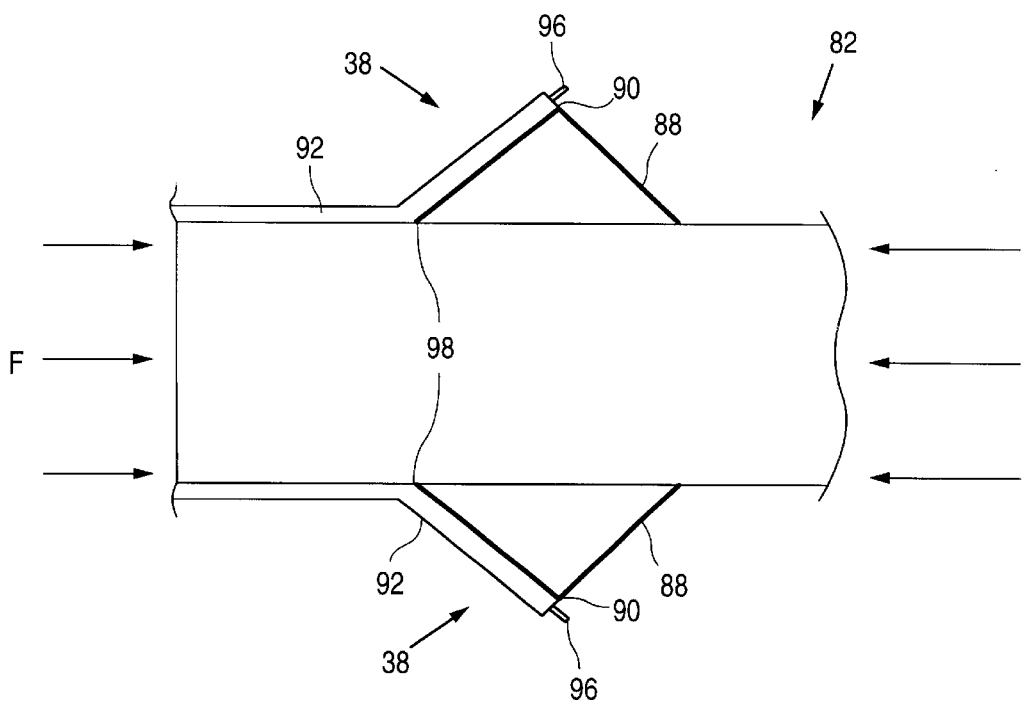

As shown in FIG. 9C, point of inflexion 90 is designed to buckle or flex when strut 88 is subjected to an axial force F. Substance delivery lumen 92 and needle 96 can be disposed on strut 88. When strut 88 is made to flex, delivery lumen 92 pivots and needle 96 rotates toward the wall of the vascular lumen. Due to the superelastic nature of struts 88, the struts force expandable member 82 to return to an original or collapsed configuration when the force is removed.

Substance delivery apparatus 80 includes at least one injection port assembly 38 or a plurality of injection port assemblies 38 for injecting a therapeutic substance into a tissue of a biological lumen. Each injection port assembly 38 includes hollow substance delivery lumen 92, which can be made from any suitable material, such as polymers and copolymers of polyamides, polyolefins, polyurethanes, and the like. Delivery lumen 92 is in fluid communication with a substance delivery sheath 94. A hollow needle 96, for penetrating into a tissue of a biological passageway, is in fluid communication with substance delivery lumen 92. The portion of needle 96 protruding from lumen 92 can be of any predetermined length, the specific length being dependent upon the desired depth of calibrated penetration and the procedure for which injection port assembly 38 is to be used. Alternatively, delivery lumen 92 and needle 96 can be replaced with a hollow needle structure, which extends the length from substance delivery sheath 94 to the point of the desired penetration.

In a first position or collapsed configuration of expandable member 82 (FIG. 9B), needle 96 of injection port assembly 38 is disposed longitudinally and substantially parallel to longitudinal axis x of expandable member 82. Substance delivery lumen 92 is capable of rotating about an elbow 98 as expandable member 82 expands. The extent of the rotation of substance delivery lumen 92 is dependent upon the degree Φ at which expandable member 82 tapers when in the expanded configuration. In one embodiment, the taper angle Φ may range from between about 0° and about 45°.

Figure 9D:
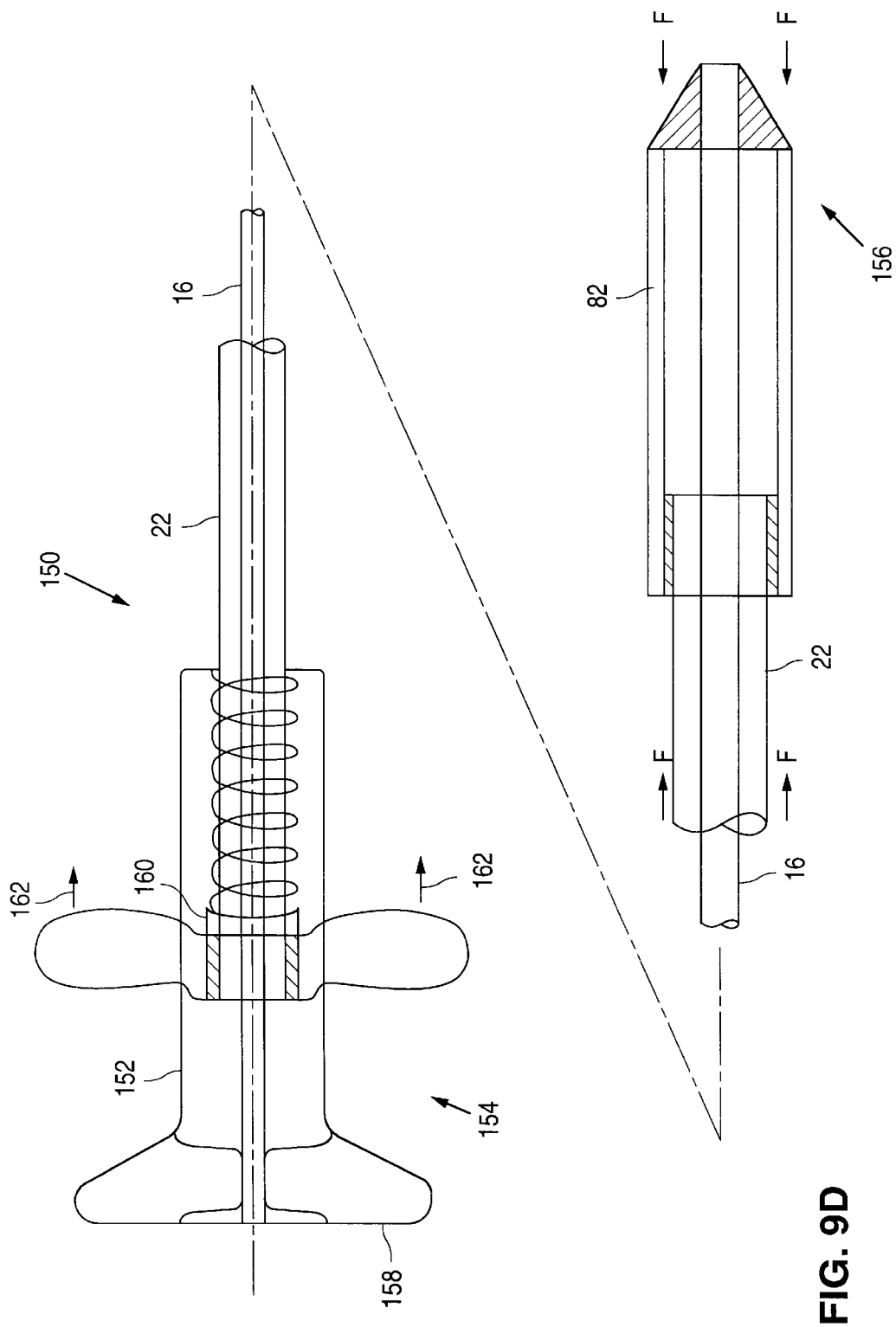

FIG. 9D is a simplified sectional view of an embodiment of a force applicator device 150 for causing tubing 82 to expand. Force applicator includes a force handle 152 disposed on a proximal end 154, with tubing 82 disposed on a distal end 156. As described above, an axial force must be applied to tubing 82 to cause struts 88 to buckle or flex to cause tubing 82 to deploy needle 96 as shown in FIG. 9C). Accordingly, force handle 152 includes a first grip 158 and a second grip 160 where each grip 158 and 160 moves relative to the other. First grip 158 is coupled to inner member 16 while second grip 160 is coupled to outer member 22.

At the proximal end of force applicator 150, inner member 16 is coupled to distal end 86 of tubing 82. Outer member 22 is coupled to distal end 84 of tubing 82. In this embodiment, the coupling of components can be accomplished using adhesives and the like that are well known to those having ordinary skill in the art.

As best understood with reference to FIG. 9D, as second grip 160 moves in the direction of arrows 162 relative to first grip 158, inner member 16 is made to move in a direction opposite to outer member 22. The result of the relative movement between inner member 16 and outer member 22 is to create a compressive force F on tubing 82. As a result, tubing 82 buckles as shown in FIG. 9C. A biasing device 164, such as a coil spring can be used to cause second grip 160 to move back to a position proximate to first grip 158. This movement causes the compressive force F to be released allowing tubing 82 to return to its original configuration.

Figure 10A:
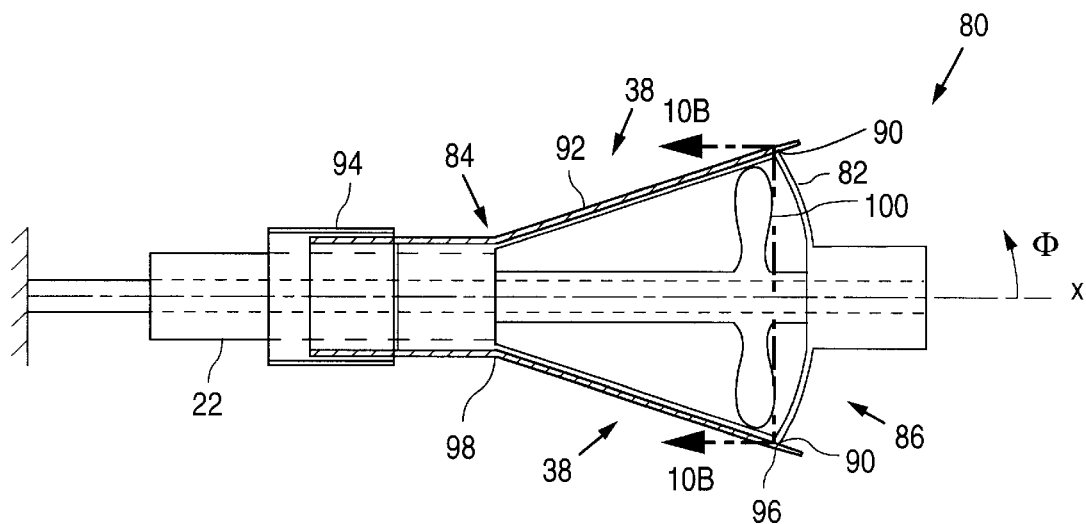
FIG. 10A is a simplified sectional view of an embodiment of the therapeutic delivery apparatus with a discoid balloon.
Figure 10B:
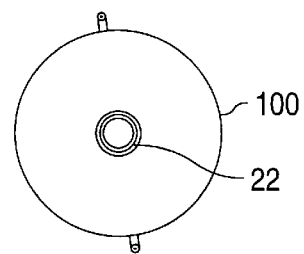
FIG. 10B is a cross-section of a the apparatus of FIG. 10A.

In another embodiment, shown in FIG. 10A, expandable member 82 can be made to expand using a discoid balloon 100. Balloon 100 is incorporated within expandable member 82 on outer member, in fluid communication with inflation lumen 22. Balloon 100 can be formed from a balloon wall or membrane, which is selectively inflatable to dilate from a collapsed configuration to a desired and controlled expanded configuration. Balloon 100 can be selectively inflated by supplying a fluid into inflation lumen 22 at a predetermined rate of pressure, for example 1–20 atm. Balloon 100 is selectively deflatable, after inflation, to return to the collapsed configuration or a deflated profile. In one example, shown in the cross-sectional view in FIG. 10B, balloon 100 is a spherical balloon with a substantially flat profile. In this example, the radial extent of the inflated balloon 100 is made to contact inflexion point 90 to cause tubing 82 to buckle and expand when balloon 100 is inflated. Alternatively, discoid balloon 100 can be used in conjunction with force applicator 150 (FIG. 9D) to aid in expanding tubing 82 and/or to provide structural support to the expanded tubing.

Figure 11A:
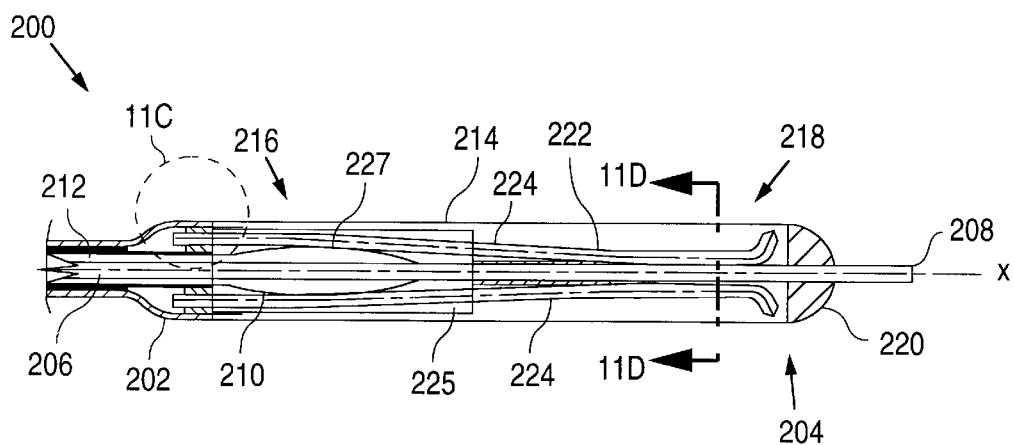
FIGS. 11A–11D are illustrations of another embodiment of the therapeutic delivery apparatus.
Figure 11C:
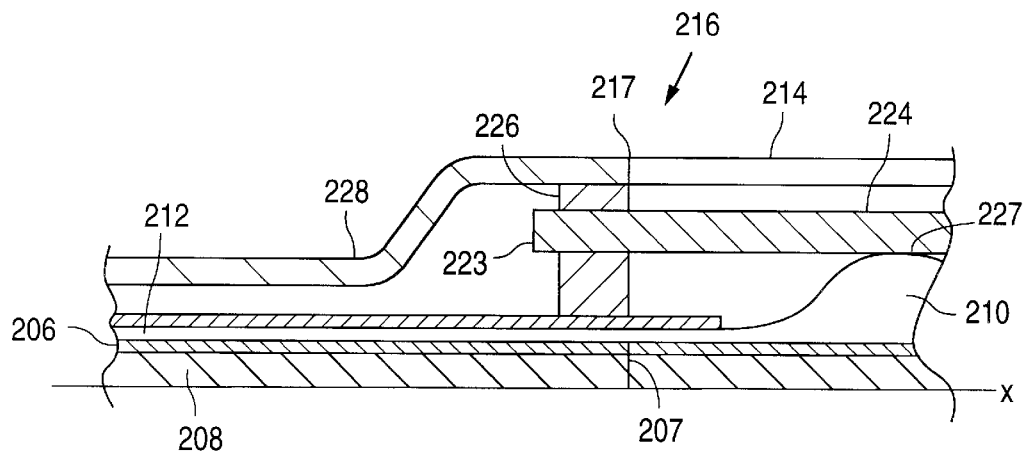
Figure 11D:
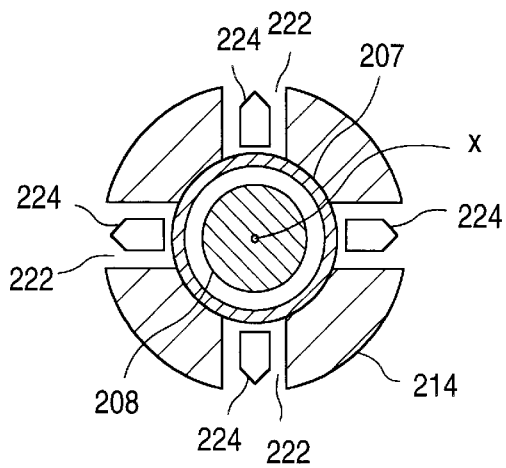
Figure 11B:
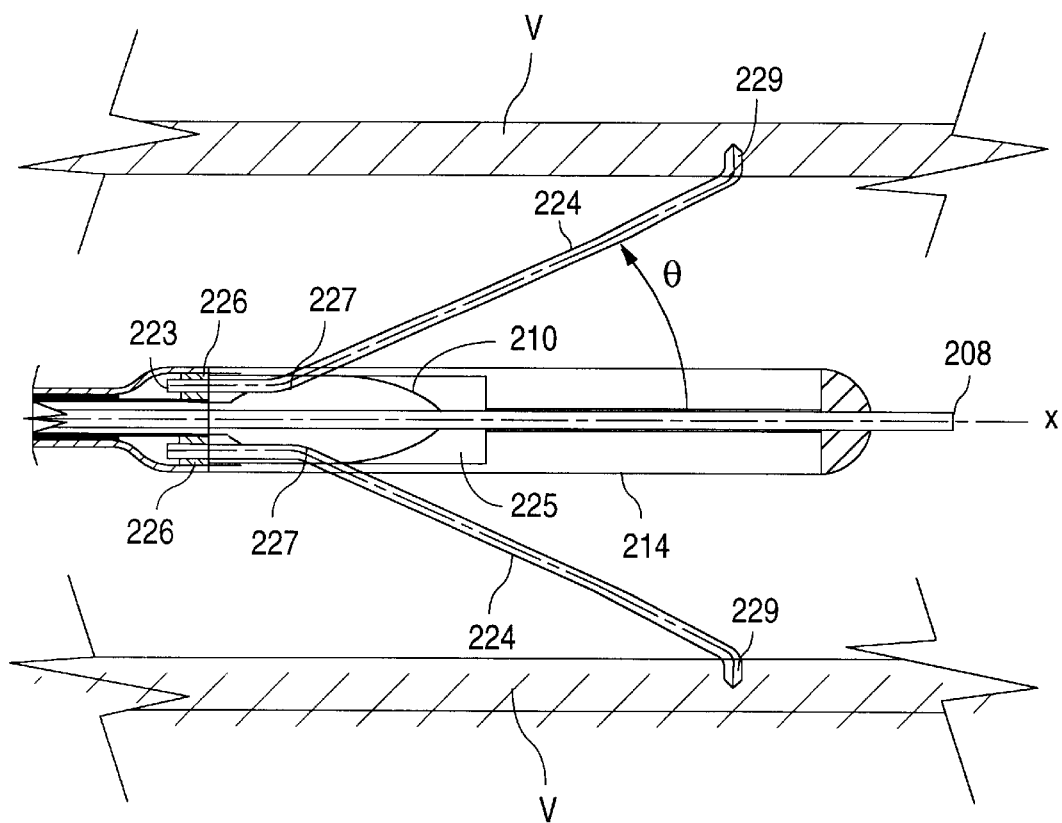

FIGS. 11A–11C are side sectional views and FIG. 11D is a cross-sectional view of another embodiment of therapeutic delivery apparatus 200. FIG. 11A shows therapeutic delivery apparatus 200, which includes a catheter assembly 202 defined by an elongated member having a proximal end (not illustrated) and distal end 204. Catheter assembly 202 can include a guidewire lumen 206 for allowing catheter assembly 202 to be fed over and maneuvered over a guidewire 208. Distal end 204 includes a housing 214 having a balloon 210 incorporated therein in fluid communication with inflation lumen 212 of catheter assembly 202. The proximal end of catheter assembly 12 includes conventional features which are well-known and understood by one of ordinary skill in the art for the proper functioning of catheter assembly 12.

Housing 214 has a proximal end 216 and a distal end 218. In one embodiment, housing 214 can be formed from a solid member of a stock alloy material, such as stainless steel or NiTi. The solid member can be fabricated into housing 214 using conventional machining, milling and similar metal removal techniques. At distal end 218 the stock solid member can be rounded 220, which facilitates insertion of housing 214 into the human vasculature. As illustrated in FIG. 11D, the stock solid member can have a bore 207, which is alignable with guidewire lumen 206 (FIG. 11A), to receive guidewire 208. The solid member also defines a plurality of elongated slots 222, formed into the stock member to extend from proximal end 216 to distal end 218, terminating at the rounded end 220. Slots 222 are sized such that slots 222 are capable of receiving therapeutic substance delivery needle 224.

As shown in FIG. 11A, proximal end 216 includes a counter-bore portion 225. Counter-bore portion 225 can extend from proximal end 216 to any length toward distal end 218, such that counter-bore portion 225 can receive balloon 210. The diameter of counter-bore portion 225 must be suitable to allow balloon 210 to substantially expand.

Accordingly, as shown in FIG. 11B, balloon 210 can be formed from a balloon wall or membrane, which is selectively inflatable to dilate from a collapsed configuration to a desired and controlled expanded configuration. While expanding, balloon 210 can cause needle 224 to move between a first position, where needle 224 is positioned within slot 222 and a second position where needle 224 is made to contact vascular lumen V. Balloon 210 can be selectively inflated by supplying a fluid into inflation lumen 212 at a predetermined rate of pressure. Balloon 210 is selectively deflatable, after inflation, to return to the collapsed configuration or a deflated profile. Balloon 210 can be made from any suitable material, as long as the specific material employed is mutually compatible with the fluids employed in conjunction with balloon 210 and able to withstand the inflation pressure developed within balloon 210. For example, balloon 210 may be made from substances including, but not limited to, polymers and copolymers of polyolefins, polyamides, polyesters, and the like.

FIG. 11C is a magnified view of a portion of hollow proximal end 216 of housing 214 in accordance with an embodiment illustrated in FIG. 11A. As illustrated in the figure, proximal end 216 of housing 214 is coupled to the remainder of catheter assembly 202 at interface 217 using conventional adhesives or else by welding. In one embodiment, a securing device 226 is positioned at interface 217 to provide support for needle 224 and to hold a first end 223 of needle 224 in communication with substance delivery lumen 228. To support needle 224, securing device 226 can include a port or hole which allows first end 223 of needle 224 to be either force fit, held with adhesive or welded to remain in fluid communication with substance delivery lumen 228. Accordingly, as therapeutic substances are provided through substance delivery lumen 228, the substances can enter into needle 224 and travel through an inner needle lumen (not shown) to be delivered to vascular wall V. Securing device 226 can be made of a metal or plastic insert, that is sealingly coupled to inflation lumen 212 at an inner diameter of the securing device and sealingly coupled to the inner wall of substance delivery lumen 228 at an outer diameter of the securing device. In this arrangement, securing device 226 prevents leakage of therapeutic substances.

A second end 229 (FIG. 11B) of each substance delivery needle 224 extends through securing device 226 and away from substance delivery lumen 228 in a cantilevered configuration. The cantilevered portion of each needle 224 extends a predetermined length, the specific length being dependent upon the desired depth of calibrated penetration and the procedure for which each substance delivery needle 224 is to be used. The cantilevered portion of each substance delivery needle 224 can be movably received within slots 222. Second end 229 includes a needle tip, which can penetrate the vascular wall V such that the therapeutic substances can be delivered therethrough. In one embodiment, the needle length can be from about 2 mm to about 10 mm. In one embodiment, substance delivery needle 224 can have an inner diameter of about 0.004" to about 0.010" and an outer diameter of about 0.006" to about 0.020".

In a first position or collapsed configuration of catheter assembly 202, housing 214 and balloon 210 (FIG. 11A), substance delivery needles 224 are disposed longitudinally within slots 222 substantially along axis x of catheter assembly 202 and housing 214 (FIG. 11D). A portion 227 of substance delivery needles 224 in close proximity to securing device 226 (i.e., proximal end 216) contacts balloon 210. Because of the cantilevered configuration of needles 224, each substance delivery needle 224 is capable of pivotally rotating with respect to securing device 226 in response to the expansion and retraction of balloon 210 within counter-bore portion 225. Thus, the dilation of balloon 210 provides a pressure sufficient to pivot each cantilevered substance delivery needle 224 an angle θ away from axis x. The extent of the rotation of substance delivery needles 224 is dependent upon the degree of expansion of balloon 210 when balloon 210 is in the expanded configuration. In one embodiment, substance delivery needles 224 may rotate between about 0° and about 45° from axis x. Once balloon 210 is inflated second ends 229 of substance delivery needles 224 are embedded in to the human vascular lumen V to deliver the desired therapeutic substance.

In the above-described embodiments, various structures in the catheter assembly can be formed from radiopaque materials so that the position of the catheter assembly may be easily observed during use. For example, needles 46 may be radiopaque. This can be accomplished, for example, by plating needles 46 with or constructing needles 46 from a radiopaque material such as titanium or tungsten. Alternatively, radiopaque materials may be placed on the catheter body near needles 46 or preferential bending points of injection port assemblies 38. Alternatively, radiopaque materials may be placed on portions of balloon 20.

The therapeutic substances discussed above can include, but are not limited to, antineoplastic, antiinflammatory, antiplatelet, anticoagulant, antifibrin, antithrombin, antimitotic, antiproliferative, antibiotic, antioxidant, antiallergic substances, and combinations thereof. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analogue from Ibsen), angiotensin converting enzyme inhibitors such as Captopril® (available from Squibb), Cilazapril® (available from Hofman-LaRoche), or Lisinopril® (available from Merck); calcium channel blockers (such as Nifedipine), coichicine, fibroblast growth factor (FGF) antagonists, fish oil (omega 3-fatty acid), histamine antagonist, Lovastatin® (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. An example of an antiallergic agent includes Permirolast potassium. Other therapeutic substances or agents which may be appropriate include alpha-interferon, genetically engineered epithelial cells, dexamethasone, and growth factors such as FGF, PDGF, and VEGF. While the foregoing therapeutic substances or agents are well known for their preventative and treatment properties, the substances or agents are provided by way of example and are not meant to be limiting. Other therapeutic substances which are currently available or that may be developed are equally applicable for use with the present invention. The treatment of patients using the above-mentioned medicines is well known to those of ordinary skill in the art.

While particular embodiments of the present invention have been shown and described, it will be obvious to those having ordinary skill in the art that changes and modifications can be made without departing from this invention in its broader aspects. Therefore, the appended claims are to encompass within their scope all such changes and modifications as fall within the true spirit and scope of this invention.

What is claimed is:

1. A catheter for delivering a therapeutic substance to a location within a vascular lumen, comprising:

an elongated member having a proximal end, a distal end, and defining a central axis;

a substance delivery lumen disposed extending along said elongated member to at least one injection port;

a surface for applying a force for causin said at least one injection port to move between a first position and a second position, wherein said injection port is substantially aligned parallel to said central axis at said first position and wherein said injection port is substantially aligned perpendicular to said central axis at said second position; wherein said surface for applying a force comprises a balloon coupled to a balloon lumen, and an elastomer sleeve surrounding at least a portion of said elongated member, at least a portion of said substance delivery lumen, and at least a portion of said balloon lumen.

2. The catheter of claim 1, wherein said elongated member comprises a guidewire lumen inner member and a balloon lumen outer member.

3. The catheter of claim 1, wherein said substance delivery lumen is disposed concentric with said elongated member.

4. The catheter of claim 1, wherein inflation of the balloon creates said force which causes said movement of said injection port.

5. The catheter of claim 1, wherein said at least one injection port comprises a plurality of injection ports.

6. The catheter of claim 1, wherein said substance delivery lumen comprises a plurality of substance delivery lumens, and wherein said at least one injection port comprises a plurality of injection ports, each of said substance delivery lumen coupled to each of said plurality of injection ports to independently provide said therapeutic substance.

7. The catheter of claim 6, wherein each of said substance delivery lumens is coupled to an independently pressurized source of said therapeutic substance.

8. The catheter of claim 1, wherein said at least one injection port is radiopaque.

9. The catheter of claim 1, wherein said at least one injection port comprises a needle.

10. The catheter of claim 1, wherein said injection port is moveable to a third position where said injection port is made to move away from said central axis.

11. A catheter for delivering a therapeutic substance, comprising:

a catheter body;

a substance delivery lumen coupled to said catheter body;

an injection port in fluid communication with said substance delivery lumen; and an inflation device for causing said injection port to move between a first position, where said injection port is substantially aligned with a central axis of said catheter body, to a second position, where said injection port is substantially aligned perpendicular to said central axis, to a third position where said injection port is made to contact an inner surface of a biological lumen.

12. The catheter of claim 11, wherein said inflation device comprises a balloon, said balloon including a plurality of tapered surfaces, each of said tapered surfaces being capable of causing independent movement of each of said injection ports.

13. The catheter of claim 11, wherein said mechanism comprises an inflatable device, wherein inflation of the inflatable device causes said movement of said injection ports.

14. The catheter of claim 11, wherein said injection ports comprise needles.

15. The catheter of claim 11, further comprising an injection port housing for housing said injection ports in said first position.

16. The catheter of claim 11, wherein said injection port is supported by a injection port lumen comprising an elbow portion about which said injection port can pivot.

17. A catheter for delivering a therapeutic substance to a location within a vascular lumen, comprising:

an elongated member defining at least one slot formed therein;

an expandable member disposed within said elongated member; and at least one injection port in contact with said expandable member to move between a first position, where said injection port is substantially within said at least one slot, and a second position, where said injection port is substantially outside of said at least one slot in response to an expansion of said expandable member; and an elastomer sleeve surrounding at least a portion of said elongated member, at least a portion said at least one injection port, and at least a portion of said expandable member.

18. The catheter of claim 1, wherein said elastomer sleeve further comprises at least one hole to allow said at least one injection port to extend therethrough.

19. The catheter of claim 1, wherein said elastomer sleeve is superelastic to provide another force for returning said at least one injection port to said first position after said at least one injection port is moved to said second position.

* * * * *

UNITED STATES PATENT AND TRADEMARK OFFICE
CERTIFICATE OF CORRECTION

PATENT NO. : 6,599,267 B1
DATED : July 29, 2003
INVENTOR(S) : Ray et al.

It is certified that error appears in the above-identified patent and that said Letters Patent is hereby corrected as shown below:

<u>Column 2,</u>
Line 34, please delete "FIG. 13" and insert -- FIG. 1B --.
Line 35, please delete "section al" and insert -- sectional --

<u>Column 12,</u>
Line 3, please delete "causin" and insert -- causing --.

Signed and Sealed this

Thirteenth Day of April, 2004

JON W. DUDAS
*Acting Director of the United States Patent and Trademark Office*